United States Patent [19]

Desbois

[11] Patent Number: 4,668,830

[45] Date of Patent: May 26, 1987

[54] PROCESS FOR THE PREPARATION OF COMPOUNDS CONTAINING A DIFLUOROMETHYLENE OR TRIFLUOROMETHYL GROUP

[75] Inventor: Michel Desbois, Rilleux, France

[73] Assignee: Rhone-Poulenc Specialites Chimiques, Courbevoie, France

[21] Appl. No.: 809,720

[22] Filed: Dec. 17, 1985

[30] Foreign Application Priority Data

Dec. 26, 1984 [FR] France ............................... 84 19799

[51] Int. Cl.$^4$ ....................... C07C 41/18; C07C 17/18; C07C 76/02
[52] U.S. Cl. ........................................ 568/655; 564/1; 564/412; 564/496; 568/56; 568/639; 568/656; 568/683; 568/936; 568/937; 568/938; 570/127; 570/165
[58] Field of Search ................ 570/165, 127; 568/655, 568/639, 656, 683, 56, 936, 937, 938; 564/496, 412, 1

[56] References Cited

U.S. PATENT DOCUMENTS

| 2,567,569 | 9/1951 | McBee et al. ................ 568/655 X |
| 4,093,665 | 6/1978 | Miller et al. ................ 568/656 X |
| 4,288,601 | 9/1981 | Kollonitsch et al. ............... 548/344 |

FOREIGN PATENT DOCUMENTS

908290 6/1962 United Kingdom .

OTHER PUBLICATIONS

Sheppard, Journal of Organic Chemistry 29, 1, 1–11, 1964.
Haas et al., Journal of Fluorine Chemistry, 20 (1982), pp. 581–587.
Prober, Jour. Amer. Chem. Soc., 75 (1953), 968–973.

*Primary Examiner*—Bernard Helfin
*Attorney, Agent, or Firm*—Finnegan, Henderson, Farabow, Garrett & Dunner

[57] ABSTRACT

A process for the preparation of compounds containing a difluoromethylene or trifluoromethyl group. A compound containing a carbonyl group, preferbly an acid, acid halide, amide, ketone or any compound containing a perhaloalkylcarbonyl moiety is placed, in anhydrous liquid hydrofluoric acid, in contact with boron trifluoride in a quantity such that the absolute pressure of boron trifluoride in the reaction system is at least one bar for a time sufficient to convert the carbonyl group to a difluormethylene or trifluoromethyl group.

The compounds obtained are useful as synthesis intermediates in the pharmaceutical, plant-protection and dye industries, as anesthetics or as heat-transfer and lubricating fluids.

15 Claims, No Drawings

PROCESS FOR THE PREPARATION OF COMPOUNDS CONTAINING A DIFLUOROMETHYLENE OR TRIFLUOROMETHYL GROUP

The present invention relates to a process for the preparation of compounds containing a difluoromethylene or trifluoromethyl group and more particularly concerns a process for the preparation of compounds containing a difluoromethylene or trifluoromethyl group which are obtained by fluorination of compounds containing a carbonyl group.

Long go, Sheppard (Journal of Organic Chemistry 29, 1, 1–11 1964) described the fluorination of acid halides by means of sulfur tetrafluoride and hyrofluoric acid. On the one hand, the preparative method employing sulfur tetrafluoride involves major limitations from the standpoint of safety, because of the very high toxicity of $SF_4$. On the other hand, $SF_4$ is not a product which is available on an industrial scale. Consequently, any industrial exploitation employing this route is to be avoided.

The method described by Sheppard has been improved by the addition of various cocatalysts such as $BF_3$, $IF_5$, and $TiF_4$ (U.S. Pat. No. 4,288,601) but these cocatalysts do not alleviate the problems of toxicity and unavailability of $SF_4$.

According to the Journal of Fluorine Chemistry 20, 518–587 (1982), it is also known to carry out the fluorination of aliphatic carbonyl or carboxyl groups by means of catalysts based on tungsten hexafluoride or molybdenum hexafluoride, occasionally in combination with boron trifluoride. These catalysts cannot be employed industrially because they are not available commercially, and they effect the replacement of the carbonyl group by a difluoromethylene group only in ketones or aldehydes.

The present invention overcomes the disadvantages of the prior art by providing a process for the preparation of compounds containing a difluoromethylene or trifluoromethyl group. A carbonyl-containing compound selected from (a) the group consisting of acids, acid halides, amides and ketones or (b) the group consisting of compounds containing a trihaloalkylcarbonyl group is placed, in anhydrous liquid hydrofluoric acid, in contact with boron trifluoride in a quantity such that the absolute pressure of boron trifluoride in the reaction system is at least about one bar. The reaction is carried out for a time sufficient to convert the carbonyl group to a difluoromethylene or trifluoromethyl group.

Representative compounds containing a carbonyl group are those of formula RCOX in which R is selected from the group (1) consisting of (a) linear or branched alkyl or haloalkyl, preferably $C_1$–$C_6$ alkyl or haloalkyl, moieties and (b) phenyl moieties optionally substituted, for example, by an alkyl, preferably $C_1$–$C_6$ alkyl, halo, alkoxy, preferably $C_1$–$C_6$ alkoxy, haloalkyl, preferably $C_1$–$C_6$ haloalkyl, phenyl, phenoxy, nitro or amino moiety, or the group (2) consisting of perhaloalkyl, preferably $C_1$–$C_2$ perhaloalkyl, more preferably trifluoromethyl, moieties.

When R is selected from the group (1) compounds, X is selected from the group consisting of hydroxy, halo, amino, alkyl, preferably $C_1$–$C_6$ alkyl, haloalkyl, preferably $C_1$–$C_6$ haloalkyl, and phenyl moieties. The phenyl moieties may optionally be substituted by alkyl, preferably $C_1$–$C_6$ alkyl, halo, alkoxy, preferably $C_1$–$C_6$ alkoxy, haloalkyl, preferably $C_1$–$C_6$ haloalkyl, phenyl, phenoxy, nitro and amino moieties.

However, when R is a group (2) perhaloalkyl compound, X is selected from the group consisting of hydroxy, halo, amino, alkyl, preferably $C_1$–$C_6$ alkyl, haloalkyl, preferably $C_1$–$C_6$ haloalkyl, phenyl (the phenyl being optionally substituted by alkyl, preferably $C_1$–$C_6$ alkyl, halo, alkoxy, preferably $C_1$–$C_6$ alkoxy, haloalkyl, preferably $C_1$–$C_6$ haloalkyl, phenyl, phenoxy, nitro and amino moieties), alkoxy, preferably $C_1$–$C_6$ alkoxy, haloalkoxy, preferably $C_1$–$C_6$ haloalkoxy, phenoxy, halophenoxy, alkylthio, preferably $C_1$–$C_6$ alkylthio, haloalkylthio, preferably $C_1$–$C_6$ haloalkylthio, phenylthio and halophenylthio moieties.

Preferred carbonyl-containing compounds are the acid halides and the esters of perfluorinated aliphatic acids, particularly the esters of trifluoroacetic acid.

Boron trifluoride ($BF_3$) presents major advantages) compared to the catalysts employed in the prior art. Unlike tungsten hexafluoride and sulfur tetrafluoride, $BF_3$ is a commercially available industrial product. In addition, $BF_3$ is advantageously a gas, which enables ready separation and recycling when the reaction is complete. Preferably, a quantity of $BF_3$ is used such that the absolute pressure of $BF_3$ in the reaction system is from about 5 to 50 bars.

Advantageously, the molar ratio of hydrofluoric acid to the derivative containing a carbonyl group is from about 5 to 50. Still more preferably, it is from 10 to 30.

The reaction temperature is preferably between 0° and 150° C. and still more preferably between 20° and 80° C.

The reaction may take place in the presence of solvents for the carbonyl-containing starting materials and/or for the compounds obtained containing a difluoromethylene or trifluoromethyl group. Illustrative solvents are $CCl_4$, $CHCl_3$ and $CFCl_2$-$CF_2Cl$.

Illustrative fluorinated derivatives obtained according to the process of the invention correspond to the formula $R'CF_2X$, in which $R'$ denotes a linear or branched alkyl, haloalkyl, aryl, such as phenyl, halophenyl, phenoxyphenyl, alkylphenyl, phenylphenyl, phenoxy, substituted phenoxy, such as halophenoxy or perhaloalkyl phenoxy, or haloalkylphenyl group, and in which X is as defined above in the formula RCOX, except that the X in RCOX is replaced by a fluorine atom from the reaction mixture when X in the formula RCOX denotes a hydroxy or halo atom other than fluorine.

The following illustrative compounds are among those obtained according to the process of the invention:

2-trifluoromethylpropane, 4-chlorotrifluoromethylbenzene, trifluoromethylbenzene, 4-nitrotrifluoromethylbenzene, 3,4-dichlorotrifluoromethylbenzene, 2-nitrotrifluoromethylbenzene, 2,6-difluorotrifluoromethylbenzene, 2-chloro-6-fluorotrifluoromethylbenzene, 4-chloropentafluoroethoxybenzene, pentafluoroethoxybenzene, α,α-difluoro-β,β,β-trichloroethoxybenzene, 4-phenoxytrifluoromethylbenzene, 3-methyltrifluoromethylbenzene, 2-methyltrifluoromethylbenzene, 4-phenyltrifluoromethylbenzene, pentafluoroethyl β,β,β-trifluoroethyl ether, α,α-difluoroethylbenzene, diphenyldifluoromethane, bis(4-fluorophenyl)difluoromethane, 4-fluoropentafluoroethoxybenzene, 3-trifluoromethylpentafluoroethoxybenzene, 4-trifluoromethylpentafluoroethoxybenzene, 2-chloro-4-trifluoromethylpentafluoroethoxybenzene, 4-trifluoromethoxypentafluoroethoxybenzene and 4-fluorotrifluoromethylbenzene.

The desired reaction products may be separated from unreacted starting materials and/or reaction byproducts by means well-known to those skilled in the art. As indicated in the following examples, gas phase chromatography may be used. Chemical means may also be used, as will be illustrated in connection with Example 1 below.

The fluorinated derivatives obtained according to the process of the invention are employed as synthesis intermediates in the pharmaceutical, plant-protection and dye industries and as anesthetics (Kirk-Othmer, 2, pp. 684–689) or as heat-transfer and lubricating fluids.

The invention will now be described in further detail in the following illustrative, non-limiting Examples.

EXAMPLE 1

100 g of anhydrous HF and 31.7 g (0.2 mol) of p-fluorobenzoyl chloride are introduced into a 250-ml stainless steel reactor stirred with a bar magnet and cooled by an ice water bath. After degassing the HCl formed, the reaction is closed, pressurized with gaseous $BF_3$ to a pressure of 20 bars (at 15° C.) and heated to 50° C. for 17 hours. After cooling and pressure release, the crude reaction mixture obtained is poured onto 200 g of crushed ice and is then extracted with 100 cm$^3$ of $CH_2Cl_2$. The collected organic phase is washed with water (2×100 cm$^3$) and is dried.

After analyses by gas phase chromatography and mass spectrometry the following composition is recorded:

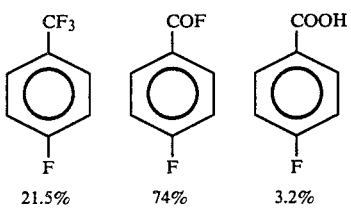

Instead of using gas phase chromatography to separate the desired reaction product from the reaction byproducts, chemical means may be used. For example, the p-fluorobenzoic acid may be neutralized by $Na_2CO_3$ and then extracted in aqueous medium. The remaining mixture of p-fluorotrifluoromethylbenzene and p-fluorobenzoic acid fluoride may be separated after condensation with an alcohol such as ethanol or butanol. The benzoic acid fluoride will be esterified by the alcohol, but the p-fluorotrifluoromethylbenzene will not be affected. The ester is then separated from the desired product by distillation.

EXAMPLE 2

100 g (5 mol) of anhydrous HF and 58 g (0.55 mol) of isobutyryl chloride are introduced in succession at 0° C. into a 250-ml stainless steel reactor fitted with a magnetic stirrer. HCl produced by the fluorination of isobutyryl chloride to isobutyryl fluoride is allowed to come off (25 min). The reactor is closed and pressurized to 10 bars with gaseous $BF_3$. The reaction is allowed to proceed for 24 hours at 50° C. After the reaction, the reactor is cooled to 0° C., the pressure is released, and the reaction mixture is poured onto 150 g of crushed ice. The solution obtained in this manner is immediately extracted with $CH_2Cl_2$ (2×100 ml).

Analyses of this organic solution, carried out by a combination of gas phase chromatography and mass spectrometry, show the presence of 2-trifluromethyl-propane (MW=112).

EXAMPLE 3

100 g of anhydrous HF and 67.2 g (0.3 mol) of p-chlorophenyl trifluoroacetate are introduced in an inert atmosphere into a 250-ml stainless steel reactor stirred with a bar magnet and cooled with an ice water bath.

The reactor is closed, pressurized to 15 bars (at 30° C.) with gaseous $BF_3$, and heated for 3 hours at 80° C. (pressure: 25 bars).

After cooling and pressure release, the crude reaction mixture obtained is poured onto 200 g of crushed ice extracted with 100 cm$^3$ of $CH_2Cl_2$.

The collected organic phase is washed with water (2×100 cm$^3$) and is dried.

After analysis by gas phase chromatography, the following composition is recorded:

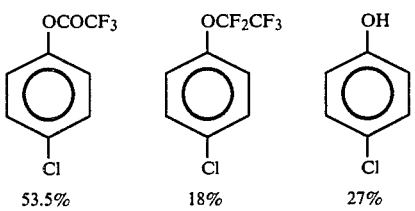

COMPARATIVE EXAMPLE NO. 3A

The following are placed in contact, by using the procedure of Example 3:

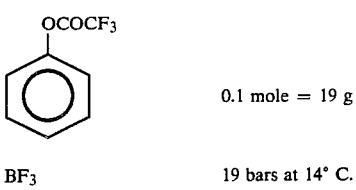

No anhydrous HF is used. The mixture is heated at 80° C. for 2 h 30 min at a maximum pressure of 24 bars $BF_3$. No trace of pentafluoroethoxybenzene is obtained.

COMPARATIVE EXAMPLE NO. 3B

The following are placed in contact, by using the same procedure as in Example 3:

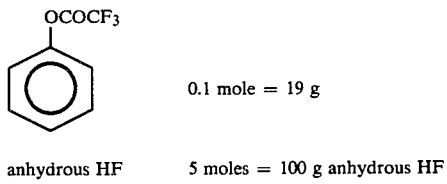

The mixture is heated at 80° C. for 23 h 30 min at a maximum pressure of 5 bars. No gaseous $BF_3$ is used.

No trace of pentafluoroethoxybenzene is obtained.

EXAMPLE 4

The procedure employed is identical to that described in Example 1, using the following materials and conditions:

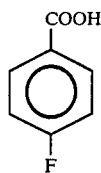

| | |
|---|---|
| | 0.1 mole = 14 g |
| anhydrous HF | 5 moles = 100 g |
| $BF_3$ | 20 bars at 20° C. |

The mixture is heated to 50° C. for 20 hours at a maximum pressure of 28 bars.

After treatment, analyses by gas phase chromatography and mass spectrometry (in combination) clearly show the presence of

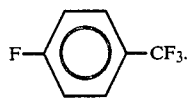

EXAMPLE 5

The procedure employed is identical to that described in Example 3, with the following conditions:

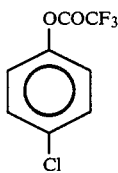

| | |
|---|---|
| | 0.2 mole = 44.9 g |
| HF | 5 moles = 100 g |
| $BF_3$ | 40 bars at 20° C. |
| T° | 20° C. |
| Time | 18 hours |

After analysis by gas phase chromatography, the followiing composition is recorded:

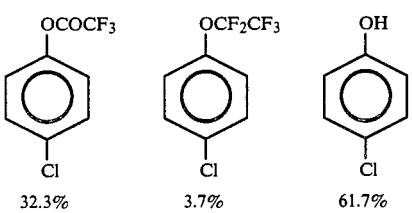

32.3%   3.7%   61.7%

EXAMPLE 6

The procedure employed is identical to that described in Example 1, with the following materials and conditions:

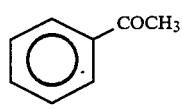

| | |
|---|---|
| | 0.1 mole = 12 g |
| anhydrous HF | 5 moles = 100 g |
| $BF_3$ | 20 bars at 20° C. |
| T° | 50° C. |
| Time | 3 h 45 min |

After treatment, analysis by fluorine-19 nuclear magnetic resonance show the presence of α,α-difluoroethylbenzene.

EXAMPLE 7

The procedure employed is identical to that described in Example 1, with the following materials and conditions:

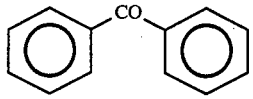

| | |
|---|---|
| | 0.1 mole = 18.2 g |
| HF anhydrous | 5 moles = 100 g |
| $CCl_4$ | 0.2 mol = 30.8 g |
| $BF_3$ | 6 bars at 20° C. |
| T° | 80° C. |
| Time | 24 hours |

After treatment, analyses by a combination of gas phase chromatography, mass spectrometry and fluorine-19 nuclear magnetic resonance show the presence of diphenyldifluoromethane (=≅5%).

EXAMPLE 8

The procedure employed is identical to that described in Example 1, with the following materials and conditions:

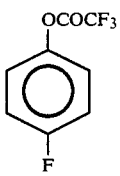

| | |
|---|---|
| | 0.2 mole = 41.6 g |
| HF | 5 moles = 100 g |
| $BF_3$ | 30 bars at 20° C. |
| T° | 40° C. |
| Time | 22 hours |

After treatment, analyses by a combination of gas phase chromatography and mass spectrometry show the presence of 4-fluoropentafluoroethoxybenzene.

EXAMPLE 9

The procedure employed is identical to that described in Example 1, with the following materials and conditions:

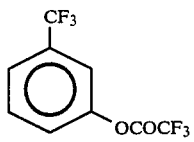

| | |
|---|---|
| | 0.15 moles = 38.7 g |
| HF | 4 moles = 80 g |
| $BF_3$ | 25 bars at 20° C. |
| T° | 50° C. |
| Time | 15 hours |

After treatment, analyses by a combination of gas phase chromatography and mass spectrometry show the presence of 3-trifluoromethylpentafluoroethoxybenzene.

I claim:

1. A process for the preparation of a compound containing a difluoromethylene or a trifluoromethyl group comprising the step of contacting a carbonyl-containing compound selected from (a) the group consisting of acids, acid halides, amides and ketones or (b) the group consisting of compounds containing a trihaloalkylcarbonyl group, in anhydrous hydrofluoric acid, with boron trifluoride in a quantity such that the absolute pressure of boron trifluoride in the reaction system is at least one bar for a time sufficient to convert the carbonyl group of said compound to a difluoromethylene or trifluoromethyl group.

2. The process of claim 1, wherein said carbonyl-containing compound has the formula RCOX, wherein R is a moiety selected from the group (1) consisting of (a) linear or branched alkyl, (b) linear or branched haloalkyl and (c) phenyl or the group (2) consisting of perhaloalkyl, wherein when R is selected from the group (1) compounds, X is selected from the group consisting of hydroxy, halo, amino, alkyl, haloalkyl and phenyl moieties, and wherein when R is selected from the group (2) compounds, X is selected from the group consisting of hydroxy, halo, amino, alkyl, haloalkyl, phenyl, alkoxy, haloalkoxy, phenoxy, halophenoxy, alkylthio, haloalkylthio, phenylthio and halophenylthio moieties.

3. The process of claim 2, wherein said R phenyl moiety is substituted by a moiety selected from the group consisting of alkyl, halo, alkoxy, haloalkyl, phenyl, phenoxy, nitro and amino.

4. The process of claim 2, wherein said X phenyl moiety is substituted by a moiety selected from the group consisting of alkyl, halo, alkoxy, haloalkyl, phenyl, phenoxy, nitro and amino.

5. The process of claim 2, wherein said compound RCOX is an acid halide or an ester of a perfluorinated acid.

6. The process of claim 5, wherein said ester of a perfluorinated acid is an ester of trifluoroacetic acid.

7. The process of claim 2, wherein said compound RCOX is selected from the group consisting of 4-fluorobenzoyl chloride, isobutyryl chloride, 7-chlorophenyl trifluoroacetate, 4-fluorobenzoic acid, 4-chlorophenyl trifluoroacetate(ester), acetophenone, benzophenone, 4-fluorophenyl trifluoroacetate and 3-trifluoromethylphenyl trifluoroacetate.

8. The process of claim 1, wherein the molar ratio of hydrofluoric acid to said carbonyl-containing compound is from about 5 to 50.

9. The process of claim 8, wherein said molar ratio is from about 10 to 30.

10. The process of claim 8, wherein said molar ratio is from about 10 to 50.

11. The process of claim 1, wherein the absolute pressure of boron trifluoride is from about 5 to 50 bars.

12. The process of claim 1, wherein the reaction temperature ranges from about 0° to 150° C.

13. The process of claim 12, wherein said temperature ranges from about 20° to 80° C.

14. The process of claim 1, wherein a solvent for said carbonyl-containing compound and/or said compound containing a difluoromethylene or a trifluoromethyl group is included.

15. The process of claim 14, wherein the solvent is selected from the group consisting of $CCl_4$, $CHCl_3$ and $CFCl_2-CF2C_1$.

* * * * *